US007118376B2

(12) United States Patent
Jodaikin et al.

(10) Patent No.: US 7,118,376 B2
(45) Date of Patent: Oct. 10, 2006

(54) SYSTEM FOR THE CONTROLLED DELIVERY OF AN ACTIVE MATERIAL TO A DENTAL SITE

(75) Inventors: Ahron Jodaikin, Kiryat Telstone (IL); Hilary Jodaikin, Kiryat Telstone (IL)

(73) Assignee: Coll Partners Ltd., (VG)

( * ) Notice: Subject to any disclaimer, the term of this patent is extended or adjusted under 35 U.S.C. 154(b) by 169 days.

(21) Appl. No.: 10/221,465

(22) PCT Filed: Mar. 14, 2001

(86) PCT No.: PCT/IL01/00243

§ 371 (c)(1),
(2), (4) Date: Jan. 6, 2003

(87) PCT Pub. No.: WO01/68038

PCT Pub. Date: Sep. 20, 2001

(65) Prior Publication Data

US 2003/0165792 A1    Sep. 4, 2003

(30) Foreign Application Priority Data

Mar. 14, 2000 (IL) .................................. 135061

(51) Int. Cl.
*A61C 19/06* (2006.01)
*A61K 7/00* (2006.01)
(52) U.S. Cl. ...................................................... 433/80
(58) Field of Classification Search .................. 433/80, 433/81, 215; 424/469, 435
See application file for complete search history.

(56) References Cited

U.S. PATENT DOCUMENTS

| 2,835,628 A | | 5/1958 | Saffir |
| 3,754,332 A | | 8/1973 | Warren, Jr. |
| 3,923,939 A | * | 12/1975 | Baker et al. .................. 264/49 |
| 4,685,883 A | * | 8/1987 | Jernberg ..................... 433/215 |
| 4,741,700 A | | 5/1988 | Barabe |
| 4,772,325 A | * | 9/1988 | Kwan et al. .................. 106/35 |
| 4,892,483 A | | 1/1990 | Douglas, Jr. |
| 5,074,786 A | * | 12/1991 | Woodward .................... 433/80 |
| 5,197,882 A | * | 3/1993 | Jernberg ..................... 433/215 |
| 5,770,182 A | | 6/1998 | Fischer |
| 5,869,096 A | * | 2/1999 | Barclay et al. .............. 424/468 |
| 5,998,431 A | * | 12/1999 | Tseng et al. ................. 514/300 |
| 6,068,859 A | * | 5/2000 | Curatolo et al. ............. 424/490 |
| 6,136,297 A | | 10/2000 | Sagel et al. |
| 6,183,775 B1 | * | 2/2001 | Ventouras ..................... 424/465 |

FOREIGN PATENT DOCUMENTS

EP        0 389 224 B1    9/1990

OTHER PUBLICATIONS

Legler, D.W. et al., "Definition, Etiology, Epidermology & Clinical Implications of Dental Carries", Menaker, L., Harper & Row, pp. 211-225, 1980.
Winston, A.E. et al., "Caries Prevention in the 21$^{st}$ Century", JADA, vol. 129, pp. 1579-1587, Nov. 1998.
Nathanson, D. et al., "In Vitro Elution Of Leachable Components From Dental Sealants", JADA, vol. 128, pp. 1517-1523, Nov. 1997.
Berry, T.C. et al., "Amalgam At the New Millennium", JADA, vol. 129, pp. 1547-1556, Nov. 1998.
Saxe, S.R. et al., "Alzheimer's Disease Dental Amalgam and Mercury", JADA, vol. 130, pp. 191-199, Feb. 1999.
Söderholm, K.J. et al., "BIS-GMA-Based Resins in Dentistry: Are They Safe?", JADA, vol. 130, pp. 201-209, Feb. 1999.
Poole, D.F.G. et al., "Remineralisation of enamel", Ciba Foundation Symposium No. 11, Elsevier Scientific Publishing Company, pp. 35-56, 1973.
Donly, K.J. et al., "Evaluating The Effects Of Fluoride-Releasing Central Materials On Adjacent Interproximal Caries", JADA, vol. 130, pp. 817-825, Jun. 1999.
Ostrom, C.A., "Fluorides in Dentistry", The Environment: Caries Prevention, Menaker L., pp. 445-460, Harper & Row, 1980.
Kautsky, M.B. et al., "Effect of Salivary Components on Dissolution Rates of Carbonated Apatites", J.D.B. Caries Res., vol. 27, pp. 373-377, Feb. 1993.
Guo, M.K. et al., "Comparison of Fluoride Uptake Produced by Tray and Flossing Methods *in vitro*", J. Dent. Res., vol. 68, pp. 496-498, Mar. 1989.
Rose, K. et al., J.Dent. Res., IADR Abs., vol. 77, p. 972, 1998.
Rawls, H.R., "Preventative Dental Materials: Sustained Delivery of Fluoride and Other Therapeutic Agents", Adv. Dent. Res., vol. 5, pp. 50-55, Dec. 1991.
Mandel, I.D., D.D.S., "Changing patterns of dental caries", Quintessence Int., vol. 16, pp. 81-87, Jan. 1985.
Massler, M., D.D.S., "Preventative Endodontics: Vital Pulp Therapy", Dental Clinics of North America, pp. 663-673, Nov. 1967.
Hoffman, S., "Histopathology of Caries Lesions", The Biological Basis of Dental Caries., Menaker L., pp. 226-246, Harper & Row, 1980.

\* cited by examiner

*Primary Examiner*—Todd E. Manahan
(74) *Attorney, Agent, or Firm*—Lerner, David, Littenberg, Krumholz & Mentlik, LLP

(57) ABSTRACT

A system for the strategic controlled delivery of materials to the dental surfaces of the intraoral cavity is disclosed. These materials have a desired or predetermined activity with respects to such dental surfaces. In particular, the system enables delivery of fluoridizing and other agents to interproximal sites among others, specially to contact points/areas (aproximal sites), to enable the prevention, treatment, diagnosis, elimination or retardation of dental caries.

55 Claims, 7 Drawing Sheets

SECTION X-X

SECTION Y-Y

FIG. 5(a)
FIG. 5(b)
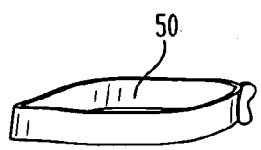
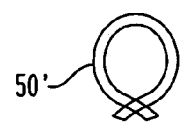
FIG. 5(c)
FIG. 5(d)
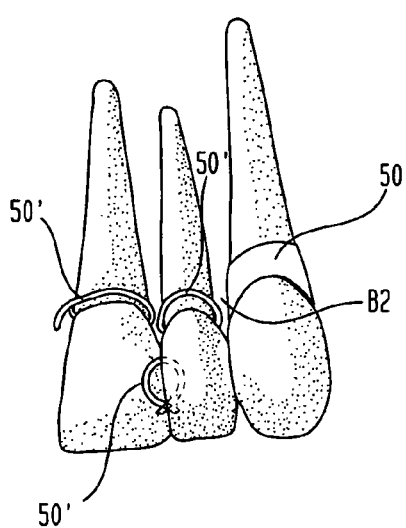
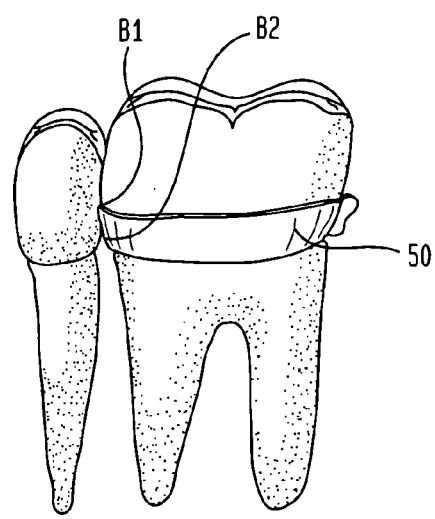

SYSTEM FOR THE CONTROLLED DELIVERY OF AN ACTIVE MATERIAL TO A DENTAL SITE

FIELD OF THE INVENTION

The present invention relates generally to the strategic delivery of materials to the dental surfaces of the intraoral cavity, in particular materials having a desired or predetermined activity with respect to such dental surfaces. More particularly, the present invention is directed at the delivery of fluoridizing and other agents to interproximal sites among others, specially to contact points/areas (aproximal sites), to enable inter alia the prevention, treatment, diagnosis, elimination or retardation of dental caries.

BACKGROUND OF THE INVENTION

Dental caries (demineralization, decay) ranks among the most significant of human diseases simply because of its frequency of occurrence in the modern world where over 90% of the population is affected, ranking dental caries first amongst the chronic diseases affecting humans in terms of the numbers of people involved. (see Poole, D. F. G. and Silverstone, L. M. in Hard Tissue Growth, Repair and Remineralisation pp 35–52 Ciba Foundation Symposium No. 11, Elsevier Scientific Publishing Company, 1973; Legler D. W. and Menaker, L. in The Biological Basis of Dental Caries; Menaker, L. pp 211–225, Harper & Row, 1980; Winston, A. E. and Bhaskar S. N. JADA 129:1579–1587, 1998, Achievements in (US) Public Health, 48(41):933, 1999).

Although the severity of this disease in terms of its life threatening potential is limited to rare instances, certain important consequences exist. Dental caries treatment is costly (requiring highly skilled and exacting manpower as well as complex biomaterials), it is time consuming, it often involves pain and discomfort (both because of sequellae and treatment); it affects aesthetics and furthermore there is a need to avoid or limit restorative dentistry because of the potential hazards of radiation, treatment and dental materials slowly degrading in the oral cavity over many years (see Nathanson, D. et al. JADA 128:1517–1523, 1997; Berry, T. C. et al. JADA 129:1547–1556,1998; Saxe, S. R. et al. JADA 130:191–199, 1999; Soderholm, K. J. and Marlott, A. JADA 130:201–209, 1999).

The major etiological factors involved in the demineralization process (dental caries) is the interplay over time of host factors (the teeth and the saliva), the microflora and the diet. Many factors can prevent dental caries such as oral hygiene, diet, fissure sealants and fluoride; the latter being the most simple, least time consuming and the most cost effective. Indeed, teeth are not dead tissue as they undergo ion exchange which determines whether there is demineralization or remineralization. The demineralization leaves the soft tooth matter porous but it has been shown that within certain limits tooth tissue may recover its original hardness after remineralization. In all cases remineralization processes are significantly enhanced by the presence of fluoride ions (Poole, D. F. G., Silverstone, L. M. in Hard Tissue Growth, Repair and Remineralisation, pp 35–52 Ciba Foundation, 1973; Donty, K. J. et al. JADA 130:817–825, 1999) for adequate periods of time or frequency (Ostrom C. A. in the Biological Basis of Dental Caries, Menaker L. 445–460, Harper & Row, 1980).

Tooth mineral consists primarily of carbonated calcium hydroxyapatite (substitutions of carbonate for a portion of phosphate in calcium hydroxyapatite) which becomes increasingly soluble as the localized pH drops. Teeth are in a constant flux of demineralization when the pH drops and remineralization when the plaque acids are neutralized by the saliva. Remineralization occurs when calcium and phosphate ions are present in adequate proportions forming hydroxyapatite which is less soluble than original carbonated calcium hydroxyapatite. However, when fluoride is present fluorapatite is formed which is even less soluble than hydroxyapatite and remineralization of carious lesions occurs when fluoride also allows the deposition of a mixture of fluoride salts. Furthermore, fluoride has antimicrobial activity itself (Ostrom, C. A. in the Biological Basis of Dental Caries, Menaker, L. 445–460, Harper & Row 1980; Kautsky, M. B. and Featherstone, J. D. B. Caries Res. 27, 373–377, 1993).

The disadvantage of current topical fluoride applications are toxicity, dilution and buffering effects of saliva, the lack of ability to reach into all susceptible sites, especially interproximally (Guo M. K. et al. J. Dent. Res. 68:496–498, 1989) and failure to penetrate through the depth of plaque and the need for relatively frequent applications. These failures are primarily governed by the lack of time that the topical fluoride can be held in the mouth and by the potential toxicity of swallowing the active agent which is used in a gross form and in relatively large amounts, even by more advanced methods (U.S. Pat. No. 5,770,182) which is also cumbersome, uncomfortable, unhygienic and fails to reach contact points or areas of teeth. An attempt to overcome some of these problems was reported by Rose K. et al J. Dent. Res. IADR Abs. 77:972, 1998. It is felt that the wedges described therein would not physically reach the contact points or areas of teeth and they would not be retained for extensive periods in a clinical situation because of physical and chemical considerations. Another approach is U.S. Pat. No. 6,136,297 which also does not deal with directly negotiating the contact points or areas, nor does an extensive literature review (Rawls, H. R. Adv. Dent. Res. 5,50–55 1991) refer to this approach. Furthermore, nor do orthodontic bands, which hold archwires onto orthodontic brackets, and release fluoride (available in the U.S.A. from Ortho-Byte) specifically target the interproximal contact points/areas. Rather, these bands release the fluoride into the saliva.

Referring to FIG. 1, there are primarily three tooth zones that are more susceptible to caries:—the fissures, marked (A), the contact points/areas (B1) (approximal zones) of interproximal regions marked (B), and the cervical margins, marked (C), which can extend into the interproximal sites at the gingival margins. Contact points exists between adjacent teeth: with aging, these points wear to form small areas of contact. Fissure sealants are reasonably effective for fissures but besides being costly and not always durable, they are not applicable to interproximal regions which are even more costly and difficult to treat. Topical fluoride applications (e.g., as in U.S. Pat. Nos. 5,770,182 and 6,136,297) are effective at cervical regions which are more prevalent today as geriatric patients have saved many of their teeth with exposed weaker dentin due to gingival recession (Mandel, ID Quintessence Int. 16,81–87 1985). However, there is a need for a more localized or targeted means of preventing microscopic cervical caries.

Dentinal caries comprises four zones, namely the infected necrotic zone, the infected superficial demineralized zone, the affected deep demineralized zone and the hypermineralized zone (Massler, M. Dental Clinics of North America pp 663–673, 1967). Although bacteria are abundant in the superficial demineralized zone only on rare occasions are a few bacteria found in the affected deep demineralized zone which comprises well formed residual tubular matrices. Indeed the major difference between this zone and sound dentin appears to be depletion of the mineral components. The clinical appearance at this zone is that of dry leathery dentinal structure (Hoffman, S. in The Biological Basis of Dental Caries. Menaker, L. pp 226–246, Harper & Row, 1980) which is the dentin collagen which may be partially denatured. Current dental treatment involves mechanically removing this layer and the more superficial layers using drills and mechanical excavation. Attempts to avoid this invasive and painful technique include air abrasion, lasers, atraumatic restorative therapy, and chemomechanical caries removal. None of these techniques have been fully accepted clinically because of a series of disadvantages and failures. This further emphasizes the need for effective preventative techniques.

An aim of the present invention is to provide a system for the controlled or sustained delivery of a material having a desired or predetermined activity to a desired dental site in the oral cavity that overcomes the disadvantages of prior art systems.

It is another aim of the present invention to provide such a system that is particularly directed to the contact points/areas of interproximal sites.

It is another aim of the present invention to provide such a system that employs a matrix as a carrier for the active material.

It is another aim of the present invention to provide such a system in which the matrix for the active material may be biodegradable, resorbable or non-resorbable.

It is another aim of the present invention to provide such a system which is particularly adapted for physical fixation onto the dental site, in particular on and/or around the interproximal contact points/areas, for at least a predetermined time period, typically sufficient to enable the controlled or sustained delivery of a required quantity of the active material from the matrix to the site.

It is another aim of the present invention to provide such a system in which fixation of the matrix is by way of a physical property of the matrix, in particular wherein the matrix comprises a hydrophilic polymer which softens and swells in situ by the hydration thereof in the oral cavity after accommodation at the dental site.

It is another aim of the present invention to provide such a system in which physical fixation of the matrix is primarily by means of a carrier member which is itself adapted on the one hand to accommodate the matrix and align the same with the dental site, and on the other hand is also adapted for affixing the carrier at the site by virtue of its shape, configuration and elasticity/resilience of the material from which it is made. In particular, such adaptation includes sufficient elasticity and toughness of the matrix material, which are important criteria when positioning the matrix between teeth.

It is another aim to provide such a system wherein the matrix is sufficiently flexible for insertion into the interproximal site, and at the same time of sufficient toughness to maintain mechanical integrity thereat, while being soft enough not to be a source of discomfort within the oral cavity.

It is another aim of the present invention to provide any one or combination of a plurality of chemical and other agents that have a desired activity at the dental site, in particular such as to enable inter alia the prevention, treatment, diagnosis, elimination or retardation of dental caries at tooth surfaces or at tooth interfaces with restorations or prostheses.

Other purposes and advantages of the invention will appear as the description proceeds.

SUMMARY OF THE INVENTION

The present invention relates to a system for the controlled delivery of at least one material having a predetermined intraoral activity to an interproximal site of at least one dental surface in an oral cavity, comprising a matrix containing said material, said matrix being adapted for affixing at said interproximal site for at least a predetermined time period correlated to the delivery of a predetermined portion of said material to said site. The interproximal site typically comprises an area of contact between said dental surface and an adjacent dental surface.

Preferably, the matrix is a polymeric matrix.

In one embodiment of the present invention, the matrix comprises a hydrophilic polymer such as to enable the matrix to be fixed by swelling in situ by the hydration thereof in the oral cavity after accommodation at said interproximal site. In particular, the polymeric matrix has a three dimensional form having at least one external surface, wherein at least a portion of said external surface is adapted for contact with at least said interproximal site of said dental surface such as to deliver said material to said site. The matrix may be in the form of a disc having at least one external substantially flat surface for contact with at least said interproximal site of said dental surface such as to deliver said material to said site. Alternatively, the matrix may be in the form of a disc having at least one external substantially concave surface for contact with at least said interproximal site of said dental surface such as to deliver said material to said site. Alternatively the matrix may be in the form of a pellet having at least one external substantially oval surface for contact with at least said interproximal site of said dental surface such as to deliver said material to said site. Alternatively, the matrix may be in the form of a toroidal ring having at least one external substantially annular surface for contact with at least said interproximal site of said dental surface such as to deliver said material to said site.

In another embodiment, the matrix is in the form of a wedge having at least one external longitudinal surface for contact with at least said interproximal site of said dental surface such as to deliver said material to said site. Alternatively, the matrix may be in the form of a wedge having at least one winged member at least at one longitudinal end thereof, said wedge having at least one external longitudinal surface for contact with at least said interproximal site of said dental surface such as to deliver said material to said site, and said winged member having suitable contact surfaces for delivering a portion of said material to a portion of said dental surface and an adjacent dental surface mesial and distal to said interproximal site.

In yet another embodiment of the present invention, the system further comprises a suitable support member for fixing said matrix to said site, said support member comprising a peripheral frame portion surrounding a net portion, said frame portion being made from a resilient material capable of enabling the support member to be accommodated at said interproximal site such as to align said net portion therewith, and wherein said net portion is adapted for accommodating said matrix and for enabling said material to be delivered therefrom to said site. The frame member may be in the form of a ring, wherein said member is attached to the inner concave surface of said ring. Optionally, the frame member further comprises at least one niche, and preferably two niches, for facilitating gripping of the said frame member to enabling affixing thereof at the interproximal site. Alternatively, the frame member may further comprise at least one loop, and preferably two, for facilitating gripping of the said frame member to enabling affixing thereof at the interproximal site. The support member is preferably made from any suitable material including natural rubber latex (cis 1,4-polyisoprene), PVC (polyvinyl chloride), Nitrile (acrylonitrile and butadiene), Neoprene (chloroprene), plastic (polyethylene) or Tactylon (styrene-based copolymers).

Optionally, the matrix may be substantially biodegradable, or resorbable or non-resorbable.

In another embodiment, the matrix is in the form of a ribbon, which may be joined in the form of a loop such as to circumscribe the periphery of a tooth comprising said dental surface and said site.

In another embodiment, the matrix is in the form of a cord, which may be joined in the form of a loop such as to circumscribe the periphery of a tooth comprising said dental surface and said site. The cord may be similar, physically and chemically, to catgut or made from any suitable material.

In another embodiment, the matrix is in the form of a cervical corset, which may be fixed with respect to said dental surface and said site by means of one or more restraining straps adapted for securing said corset to a tooth comprising said dental surface. The straps typically circumscribe at least a portion of said tooth.

In another embodiment, the matrix is in the form of an orthodontic interproximal "I" device, which may be fixed with respect to said dental surface and said site by means of an orthodontic arch wire previously secured in the intraoral cavity for securing said "I" device to a tooth comprising said dental surface.

In a further aspect, the present invention also relates to a system for the controlled delivery of a material having a predetermined intra oral activity to an occlusal site of at least one dental surface in an oral cavity, comprising a matrix containing said material; said matrix being adapted for affixing at said occlusal site for at least a predetermined time period correlated to the delivery of a predetermined portion of said material to said site. In one embodiment, the matrix is in the form of an occlusal corset, which may be affixed with respect to said dental surface and said site by means of one or more restraining straps adapted for securing said corset to a tooth comprising said dental surface. Preferably, the straps circumscribe at least a portion of said tooth, and at least one said strap circumscribes at least a portion of an adjacent tooth.

For all embodiments, the active material may be, for example, any one of inorganic or organic fluoride-containing chemical agent. The material may be any one of sodium fluoride, stannous fluoride, stannous hexafluorozirconate, calcium fluoride, difluorosilane, hydrogen fluoride, sodium monofluorophosphate, ytterbium trifluoride, sodium hexafluorosilicate, ammonium fluoride, an amine fluoride, fluoroaluminosilicate glass and any mixture thereof.

The matrix may comprise a synthetic polymer or a natural polymer which may be at least one of polysacaccharides, lipids, polyisoprene, gum and proteins, or any mixture thereof. The natural polymer may be a protein selected from collagen and gelatin. Preferably, the polymer is cross-linked, typically by at least one of glutaraldehyde, formaldehyde, glycol dimethacrylate, tannic acid and allyl methacrylate.

The matrix optionally further comprises an auxiliary agent which may be any one of an enhancing agent for enhancing the release of the active material, plasticizer, elasticizer, coloring and staining agent, fillers and softeners, and preserving and sterilizing agents. Such a plasticizer may be sorbitol.

The present invention also relates to a support member for fixing a polymeric matrix comprising a material having a predetermined intraoral activity to an interproximal site of at least one dental surface in an intraoral cavity, said support member comprising a peripheral frame portion surrounding a net portion, said frame portion being made from a resilient material capable of enabling the support member to be accommodated at said interproximal site such as to align said net portion therewith, and wherein said net portion is adapted for accommodating said matrix and for enabling said material to be delivered therefrom to said site. In one embodiment, the frame member is in the form of a ring, wherein said member is attached to the inner concave surface of said ring. The frame member optionally further comprises at least one niche for facilitating gripping of the said frame member to enabling affixing thereof at the interproximal site. Alternatively, the frame member further comprises at least one loop for facilitating gripping of the said frame member to enabling affixing thereof at the interproximal site. Typically, the support member is made from any suitable material including natural rubber latex (cis 1,4 polyisoprene), PVC (polyvinyl-chloride), Nitrile (acrylonitrile and butadiene), Neoprene (chloroprene), plastic (polyethylene) or Tactylon (styrene-based copolymers).

BRIEF DESCRIPTION OF THE FIGURES

FIG. 5(a) is a side, perspective view of a fourth embodiment of the present invention;

FIG. 5(b) is a front, perspective view of another embodiment of the present invention;

FIG. 5(c) is a side, elevational view of a portion of the interior teeth and the posterior teeth, respectively, illustrating the configurations of FIGS. 5(a)–5(b), fixed in situ with respect to a cervical and interproximal zone.

FIG. 5(d) is a side, elevational view of a portion of the interior teeth and the posterior teeth, respectively, illustrating the configurations of FIGS. 5(a)–5(b), fixed in situ with respect to a cervical and interproximal zone.

DETAILED DESCRIPTION

The present invention is defined by the claims, the contents of which are to be read as included within the disclosure of the specification, and will now be described by way of example with reference to the accompanying Figures.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The present invention relates to a system for the controlled or sustained delivery of a material having a predetermined intra-oral activity to a dental site of the oral cavity, typically on tooth surfaces or carious lesions, and in particular to contact points/areas of an interproximal site of at least one dental surface of the oral cavity, the system comprising a matrix containing said material. The matrix is adapted for the controlled or sustained release of the active material, and is further adapted for fixation at the dental site, and in particular the interproximal site, for at least a predetermined time period that is correlated to the delivery of a predetermined portion of said material to said site. This time period typically depends on the nature of the active material and on the subject being treated, and may comprise about four hours or indeed even about four days, for example, when fluoridizing an interproximal site according to the present invention. It is to be appreciated that a major factor in establishing the rate of release of the active material is the structure of the polymeric matrix. Thus, desired rates of release may be achieved by employing specific polymers, which are preferably cross-linked to a degree affording the desired rate of release. Matrices that are highly cross-linked would release the active material more slowly, and vice versa. The man of skill in the art of pharmacy and delivery system is familiar with such considerations, which are described in many articles and textbooks, e.g., Remington's Pharmaceutical Sciences, Gennaro A. R. ed., Mack Publishing Company, Easton, Pa., 1990, which is fully incorporated herein by reference.

Figure 1A:
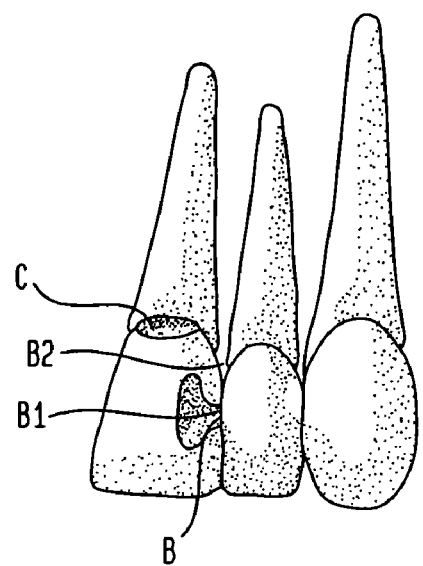
FIG. 1(a) is a side, elevational view of a labial portion of the anterior teeth and the posterior teeth, respectively, illustrating the three major tooth zones that are particularly susceptible to dental caries.
Figure 1B:
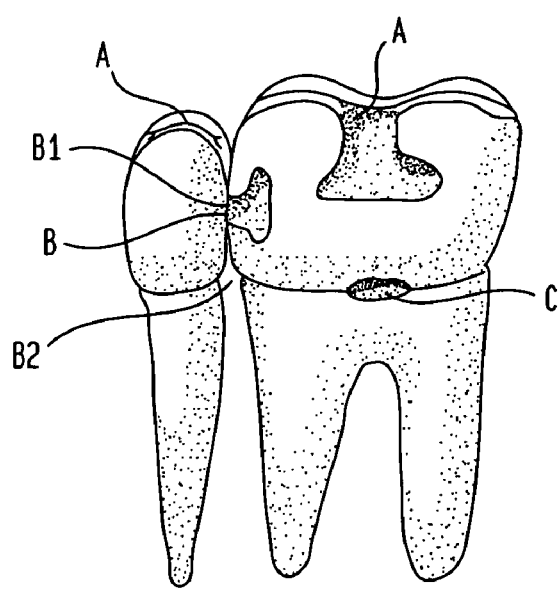
FIG. 1(b) is a side, elevational view of a buccal portion of the anterior teeth and the posterior teeth, respectively, illustrating the three major tooth zones that are particularly susceptible to dental caries.

Referring to FIG. 1(a) and FIG. 1(b), the interproximal site (B) comprises a point/area (B1) of contact between a dental surface of interest, i.e., wherein it is desired to deliver the active material, and an adjacent dental surface. The interproximal site (B) also comprises a space (B2) where the adjacent teeth do not touch. According to the present invention, said active material may be delivered to the point/area of contact (B1) and/or space (B2) where the teeth do not make direct contact, and to either one or both of the adjacent teeth.

Figure 2A:
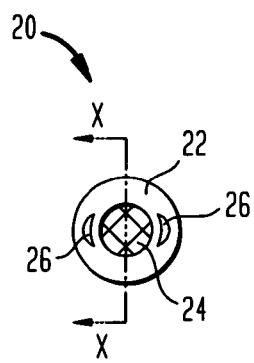
FIG. 2(a) is a front, elevational view of a first embodiment of the present invention.
Figure 2B:
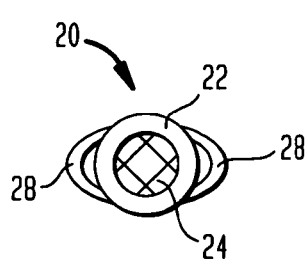
FIG. 2(b) is a front, elevational view of another embodiment of the present invention.
Figure 2C:
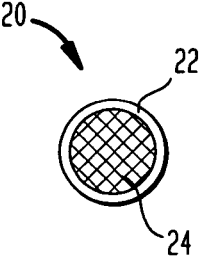
FIG. 2(c) is a front, elevational view of another embodiment of the present invention.
Figure 2D:
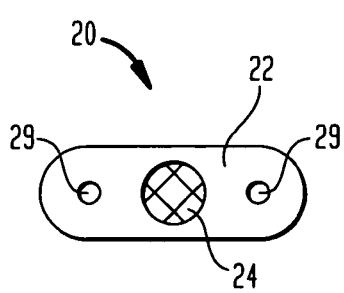
FIG. 2(d) is a front, elevational view of another embodiment of the present invention.
Figure 2E:
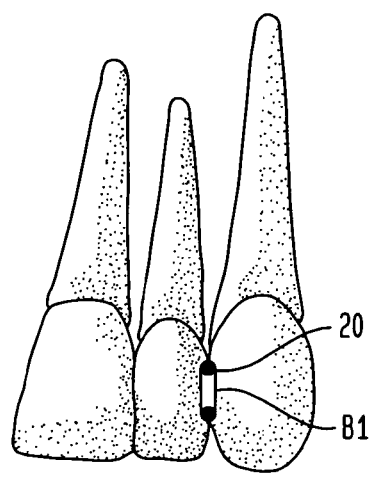
FIG. 2(e) is a side, elevational view of a portion of the interior teeth and the posterior teeth, respectively, illustrating the configurations of FIGS. 2(a) and 2(d) fixed in situ with respect to an interproximal zone.
Figure 2F:
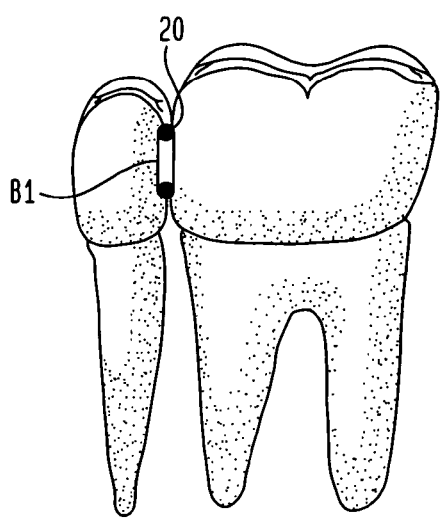
FIG. 2(f) is a side, elevational view of a portion of the anterior teeth and the posterior teeth, respectively, illustrating the configurations of FIGS. 2(a) and 2(d) fixed in situ with respect to an interproximal zone.
Figure 2G:
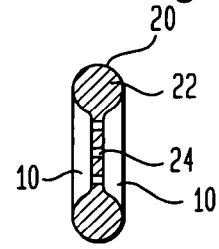
FIG. 2(g) is a side, elevational, cross-sectional view of the embodiment of FIG. 2(a) taken along line X—X thereof.

In a first embodiment if the present invention, and referring to FIGS. 2(a) to 2(g), the delivery system comprises a polymeric matrix (10) containing the active material, and a suitable carrier or support member (20) for fixing said matrix (10) to the desired interproximal site, typically the point/area of contact (B1) thereof. The said support member (20) comprises a peripheral frame (22) surrounding a net portion (24). The frame portion (22) is typically made from a resilient material capable of enabling the support member (20) to be accommodated at the corresponding area of contact (B1) of the interproximal site (B) such as to align said net portion (24) therewith, as illustrated in FIGS. 2(e) and 2(f). The net portion (24) is adapted for accommodating and retaining the said matrix (10) and for enabling the active material contained therein to be delivered from the matrix (10) to the site (B). Furthermore, the net portion (24) also facilitates the positioning of the matrix at the interproximal site. Thus, the net portion (24) acts as a retentive, receiving vessel or seat for the matrix (10) affixing the matrix to the support member (20). At the same time the plurality of apertures or orifices comprised in the net portion (24) also enables the active material to be delivered to both adjacent teeth at the area of contact (B1), as illustrated in FIGS. 2(*a*) to 2(*d*).

Referring to FIG. 2(*a*), in a first configuration of the support member (20), the frame member (22) is substantially ring-like or annular, wherein said net member (24) is attached to the inner cylindrical or concave surface of the ring. In the first configuration, the frame member (22) also comprises a pair of diametrically opposed niches (26) for the purpose of positioning the support member (20) in between the teeth. This is accomplished by placing the beaks of a rubber dam pliers, orthodontic pliers, a custom designed pliers, dental floss, or any other apparatus which stretches the member (20) in order to maneuver it interproximally.

A second configuration of the first embodiment, illustrated in FIG. 2(*b*), comprises the same elements as described hereinbefore with respect to the first configuration, mutatis mutandis, with the exception that instead of the niches (26), the frame member (22) also comprises a pair of diametrically opposed loops (28) extending from the outer rim of the frame member (22) for the purpose of placing the support member (20) in-between adjacent teeth, as for the first configuration. However, the loops (28) have an additional advantage in that wider beaks may be used, and in that they are also enable the support member (20) to be stretched by hand.

A third configuration of the first embodiment, illustrated in FIG. 2(*c*), comprises the same elements as described hereinbefore with respect to the first configuration, mutatis mutandis, with the exception that the net member comprises a smaller mesh than in the first configuration, and furthermore lacks the said niches (26).

In a fourth configuration of the first embodiment, illustrated in FIG. 2(*d*), the frame member is in the form of a strip having a centrally disposed circular aperture, wherein said net member (24) is attached to the inner cylindrical or concave surface of the aperture. In the fourth configuration, the frame member (22) also comprises a pair of diametrically opposed niches (29) aligned along the length of the strip for the purpose of placing the support member (20) in-between adjacent teeth, as for the first configuration. However, the additional length afforded by the strip facilitate placement by hand.

In the first embodiment of the present invention, the frame member (22) is typically integral with the net member (24) and may be made as a molded item from any suitable materials that facilitate placement of the active material within the support member (20) and to enable the support member (20) to be easily slipped in between the teeth. Such suitable materials may include natural materials such as, for example, natural rubber latex (cis 1,4 polyisoprene), or synthetic materials such as, for example, PVC (polyvinylchloride), Nitrile (acrylonitrile and butadiene), Neoprene (chloroprene), plastic (polyethylene) or Tactylon (styrene-based copolymers made by the Safeskin Corporation). Placement of the support member (20) including the matrix (10) may be accomplished by stretching the support member (20) by hand, with floss, with a rubber dam pliers, orthodontic pliers, or a custom designed pliers with optimally shaped beaks. As the support member (20) typically needs to be stretched into about 4–5 times its unstressed diameter, the physical properties of the active material and in particular the matrix (10) will have to include suitable elastic properties which match that of the elastic support member (20). Other shapes, for example oval or square, are also within the scope of the invention. The net portion (24) can vary in the mesh open area provided thereby, and may be made from the same material as the frame member (22) or from a different material thereto, for example, such as nets or fibrefilms used in triple impression trays.

The first and third configurations may comprise an external diameter ranging, typically, between 3 mm and 9 mm, particularly between about 3.8 mm and 4.6 mm. The external dimension of the second configuration may be similar, not including the loops (28), and so too the width of the fourth configuration.

The first embodiment may thus be used to remineralize demineralized interproximal regions of teeth which have been detected visually or radiologically. Further, a programmed prevention technique can be used to strategically fluoridate teeth as they erupt.

When orthodontic separation of teeth is to be instituted, the first embodiment may be conveniently used to provide preventive fluoridization of the interproximal regions.

According to the first embodiment of the present invention, it may be necessary to separate the teeth using orthodontic techniques, in order to position the support member and matrix therein. However, such a separation is typically much less than in regular orthodontic practice.

Thus, in the first embodiment of the present invention, the support members are formed such as to embody the appropriate shape to contact the tooth surface and retain its position as well as to facilitate ease of application in the targeted areas by embodying adequate elasticity and toughness for the contact areas or points. Hence a wide range of shapes can be manufactured, for example in predesigned moulds (e.g. of plastics, metal or rubber) where the chemical components (including the matrix and active material) are placed or injected and set, using chemical and/or physical means (e.g. chemical interactions, concentration changes, pressure, temperature and/or irradiation). Another example is the production of sheets of a suitable material from which desired shapes of the support member can be cut or punched out. The support members, for example as exemplified in FIGS. 2(*a*) to 2(*e*), may be produced in the form of individual members, or alternatively attached to a "mother" branch or branches. These branches comprising the support members can then be treated with the active material, such as for example remineralizing agent, itself by flowing the wet or liquid material into the retention portions of these members and then dried or set. In accordance with further embodiment of the present invention, any alternative suitable technique may be used to produce the device or the material.

Alternatively, the support member of the first embodiment may be adapted for carrying the matrix at a micro-scale. In such a configuration, the support member is made from a suitable porous material, having pores, tubules or any other micro-scale structures for containing the matrix, rather than the net portion for accommodating the matrix. The active material is then released from the pores and to the interproximal site. Such pores/tubules may be provided by laser drilling techniques applied to a support member made from regular latex rubber. Alternatively, during the manufacturing process of the support member, air or any suitable gas may be introduced to the molten latex rubber at suitable temperature/pressure to form a cellular or porous structure therein when set.

While the support member of the first embodiment is preferably made from non-resorbable materials such as latex rubber, for example, the support member may nevertheless be made, alternatively, from resorbable and/or biodegradable materials that are typically more resilient or durable than the material of the matrix itself. For example, the support member may be made from the same basic material as the matrix, but cross-linked by cross-linking agents that are stronger, or more concentrated, or agents other than used for cross-linking the matrix.

In a second and third embodiments according to the present invention, and in fact also in the first embodiment, the matrix is a polymeric matrix, which may be biodegradable, resorbent or non-resorbent, and comprises a hydrophilic polymer such as to enable the matrix to be retained in place, optimizing surface contact by swelling in situ by the hydration thereof in the oral cavity after accommodation at said interproximal site. Furthermore, the polymeric matrix has a three dimensional form having an external surface, wherein at least a portion of said external surface is adapted for contact with one of the two adjacent teeth, at the contact point/area (B1) and/or the non-contact space (B2) of the interproximal site (B), such as to deliver said material to said site. Alternatively, the three dimensional form of the matrix has two distinct surfaces, a first external surface and a second external surface. In the latter case, at least a portion of said first external surface is adapted for contact with dental surface of one tooth at the area of contact (B1) and/or the space (B2) of said interproximal site (B), and at least a portion of said second external surface is adapted for contact with the dental surface of the adjacent tooth at the area of contact (B1) and/or the space (B2), such as to deliver the active material to both adjacent teeth at the interproximal site (B). As with the first embodiment, the adjacent teeth are actually separated at area of contact (B1) when the delivery system is fixed in place.

Figure 3A:
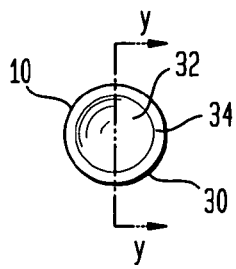
FIG. 3(a) is a front, elevational view of a second embodiment of the present invention.

Thus, in the second embodiment, and referring to FIG. 3(a) the polymeric matrix is particularly adapted for providing the active material to the contact area (B1).

Figure 3B:
FIG. 3(b) is a front, elevational view of another embodiment of the present invention.
Figure 3C:
FIG. 3(c) is a front, elevational view of another embodiment of the present invention.
Figure 3D:
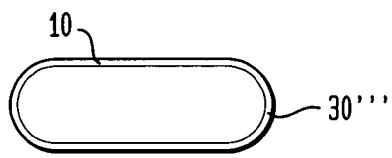
FIG. 3(d) is a front, elevational view of another embodiment of the present invention.
Figure 3E:
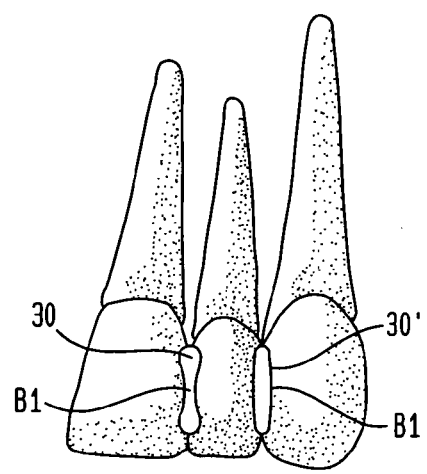
FIG. 3(e) is a side, elevational veiw of a portion of the interior teeth and the posterior teeth, respectively, illustrating the configurations of FIGS. 3(a)–3(d) fixed in situ with respect to an interproximal zone.
Figure 3F:
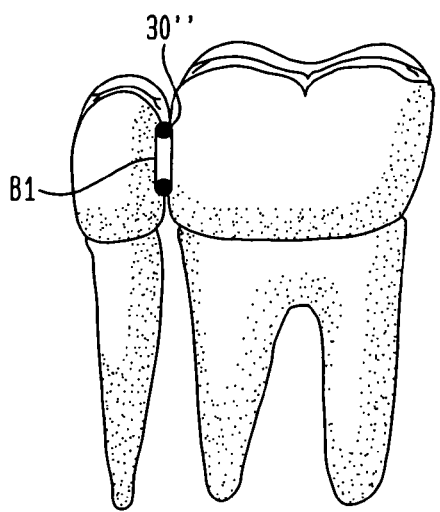
FIG. 3(f) is a side, elevational view of a portion of the interior teeth and the posterior teeth, respectively, illustrating the configurations of FIGS. 3(a)–3(d) fixed in situ with respect to an interproximal zone.
Figure 3G:
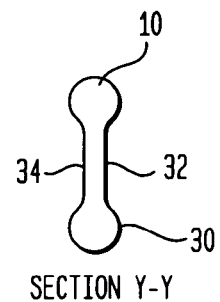
FIG. 3(g) is a side, elevational, cross-sectional view of the embodiment of FIG. 3(a) taken along line X—X thereof.

In a first configuration of the second embodiment, and referring to FIGS. 3(a) and 3(g), the polymeric matrix (10) is in the form of a disc (30) having opposed first and second external substantially concave surfaces, (32) and (34) respectively, for contact with at least the contact area (B1) of said dental surfaces of the adjacent teeth at the of the interproximal site (B) such as to deliver said material to said site.

In a second configuration of the second embodiment, and referring to FIG. 3(b), the polymeric matrix (10) is in the form of a disc (30') having opposed first and second external substantially flat surfaces, for contact with at least the contact area (B1) of said dental surfaces of the adjacent teeth at the of the interproximal site (B) such as to deliver said material to said site In a third configuration of the second embodiment, and referring to FIG. 3(c), the polymeric matrix (10) is in the form of a ring (30") having opposed first and second external substantially annular surfaces, for contact with at least the contact area (B1) of said dental surfaces of the adjacent teeth at the of the interproximal site (B) such as to deliver said material to said site.

In a fourth configuration of the second embodiment, and referring to FIG. 3(d), the polymeric matrix is in the form of a longitudinal strip or pellet (30'") having opposed first and second external substantially oval surfaces, for contact with at least the contact area (B1) of said dental surfaces of the adjacent teeth at the of the interproximal site (B) such as to deliver said material to said site. This elongated configuration facilitates stretching by hand for positioning of the matrix interproximally.

Where necessary, a dental practitioner may pry adjacent teeth apart using, for example, a wooden wedge, or a metal separating device, in order to facilitate placement of the system therebetween. Thereafter, the wedge or separating device is removed.

Thus, in the second embodiment of the present invention, the polymeric matrix (10) is anatomically shaped to fit the interproximal anatomy of the teeth in order to reach the contact points or areas, for the slow release of the active material, typically fluoride and/or other agents, as illustrated in FIGS. 3(e) and 3(f).

In the first, second, third and fourth configurations of the second embodiment, the external diameter may range, typically, between 3 mm and 9 mm, particularly between about 3.8 mm and 4.6 mm. Also, other shapes, for example oval or square, are also within the scope of the invention.

Figure 4A:
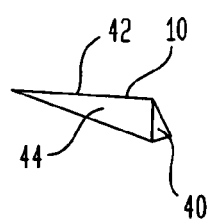
FIG. 4(a) is a front, elevational view of a third embodiment of the present invention.
Figure 4B:
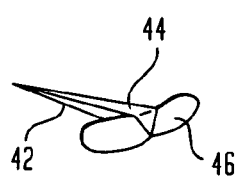
FIG. 4(b) is a front, perspective view of another embodiment of the present invention.
Figure 4C:
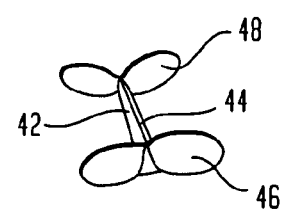
FIG. 4(c) is a front, perspective view of another embodiment of the present invention.
Figure 4D:
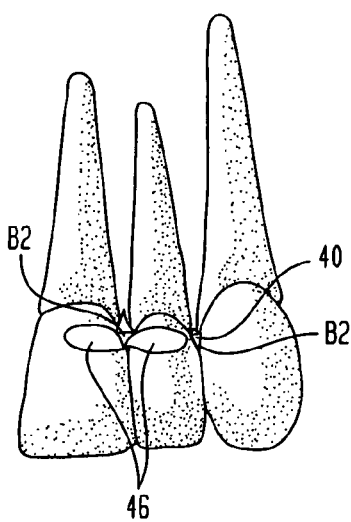
FIG. 4(d) is a side, elevational view of a portion of the interior teeth and the posterior teeth, respectively, illustrating the configurations of FIGS. 4(a)–4(c) fixed in situ with respect to an interproximal zone.

In the third embodiment, and referring to FIGS. 4(a) to 4(e) the polymeric matrix is particularly adapted for providing the active material to the space (B2). In a first configuration of the third embodiment, and referring to FIG. 4(a), the polymeric matrix (10) is in the form of a wedge (40) having first and second external substantially longitudinal surfaces, (42) and (44) respectively, for contact with at least the facing dental surface of the adjacent teeth at the interproximal space (B2) at the of the interproximal site (B) such as to deliver said material to said site, close to the gingiva and towards the contact point/area, as illustrated in FIG. 4(d).

Figure 4E:
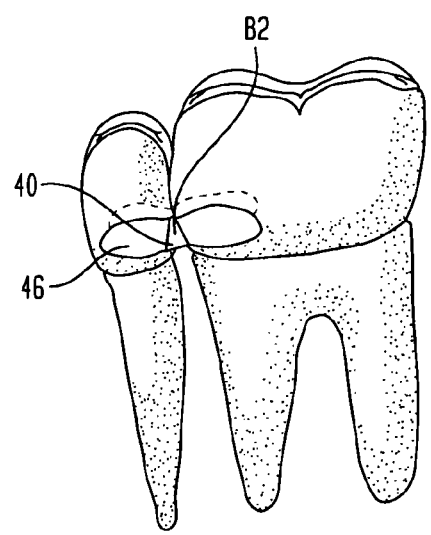
FIG. 4(e) is a side, elevational view of a portion of the anterior teeth and the posterior teeth, respectively, illustrating the configurations of FIGS. 4(a)–4(c) fixed in situ with respect to an interproximal zone.

In a second configuration of the third embodiment, and referring to FIG. 4(b), the polymeric matrix is in the form of a wedge (40) having a one pair of winged members (46) at one longitudinal end thereof. Alternatively, the wedge (40) may comprise a winged member (46) at one longitudinal end thereof directed towards only one of the two adjacent teeth. As with the first configuration, the wedge (40) has first and second external substantially longitudinal surfaces, (42) and (44) respectively, for contact with at least the facing dental surface of the adjacent teeth at the space (B2) at the of the interproximal site (B) such as to deliver said material to said site. Each of the winged members also have suitable contact surfaces which wrap around and deliver a portion of said material to a portion of externally facing dental surfaces of the of the cervical regions of the two adjacent teeth, mesial and distal to said interproximal site. The winged members may optionally be long enough to wrap around each corresponding tooth and into the next interproximal site, as illustrated in FIGS. 4(d) and 4(e).

A third configuration of the third embodiment, and referring to FIG. 4(c) comprises all the elements described for the second configuration of the third embodiment, mutatis mutandis. Furthermore, the matrix in the third configuration of the third embodiment also comprises a second pair of winged members (48) at the other longitudinal end of the wedge (40). Alternatively, the wedge (40) may comprise a winged member (46) at the second longitudinal end thereof directed towards only one of the two adjacent teeth. Each of the winged members (48) also have suitable contact surfaces for wrapping around and delivering a portion of said material to a portion of the internally facing dental surfaces of the cervical regions of the two adjacent teeth, proximal and distal to said interproximal site. Thus, the third configuration of the third embodiments is in the form of an interproximal "I" device which has its arms, i.e. the winged elements, folded to slip between the teeth before the arms are allowed to "spring" into the original position.

Thus, according to the second and third embodiments, the matrices are formed as small appropriate anatomically shaped configurations.

Optionally, other embodiments of the present invention may comprise a combination of the embodiments described herein. For example, another embodiment of the present invention may comprise a matrix in the form of a disk, similar to that of the second embodiment, formed integrally with a wedge member, similar to that of the third embodiment, fixed at a circumferential perimeter of the disk. Thus, areas (B1), (B2) and (C) may be dealt with using the same matrix body.

In the fourth embodiment of the present invention, the said matrix is in the form of a ribbon or cord which may be impregnated with the active material and which is further adapted for enabling the material to be released in a controlled or sustained manner by intra-oral bio-degradation.

In a first configuration of the fourth embodiment, and referring to FIG. 5(a), the matrix is in the form of a ribbon (50) that may be joined—integrally, by means of a knot or in any other manner—in the form of a loop such as to circumscribe the periphery of a tooth comprising said dental surface and the site that is being targeted for treatment, in particular the enamel and/or dentin at the cervical regions and may also include part of the interproximal regions, as illustrated in FIG. 5(c). The ribbon (50) may be made from any suitable materials, as described hereinbelow.

In a second configuration of the fourth embodiment, and referring to FIG. 5(b), the matrix is in the form of a cord (50') that may be joined—typically by tying together the ends of a length thereof—in the form of a loop such as to circumscribe the periphery of a tooth comprising said dental surface and said interproximal site, as illustrated in FIGS. 5(c) and 5(d). The cord (50') may be similar to catgut or made from any suitable materials, as described hereinbelow.

Typically, in the fourth embodiment, the ribbon (50) or cord (50') may be cut to a required length from a roll thereof, and may vary in size and shape, cross-sectional profile, and so on.

In the fifth embodiment of the present invention, the matrix is in the form of a corset, typically a cervical corset (60) or an occlusal corset (60') and in the form of straps (62) fixed thereto. These corsets and straps may be made from any suitable materials, as described hereinbelow, and enables the active material contained therein to be released in a sustained or controlled manner to the desired surface.

Figure 6A:
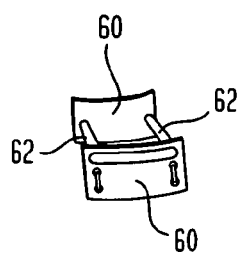
FIG. 6(a) is a side, perspective view of a fifth embodiment of the present invention.

In a first configuration of the fifth embodiment, and referring to FIG. 6(a), a cervical corset (60) is provided for placements around the neck of teeth with or without gingival recession. The cervical corset (60) may be fixed with respect to said dental surface and said site by means of one or more restraining strings or straps (62) which are adapted for securing said corset to a tooth comprising said dental surface. The straps (62) circumscribe at least a portion of said tooth, in particular passing through the interproximal region (B) of the adjacent teeth, as illustrated in FIG. 6(c). The straps are typically made from any suitable material as described hereinbelow, serving as a matrix for delivering the active material to the interproximal site (B), as well as to the cervical site (C).

Figure 6B:
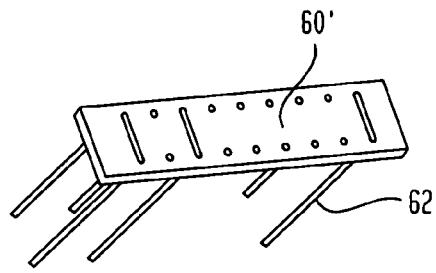
FIG. 6(b) is a front, perspective view of another embodiment of the present invention.
Figure 6C:
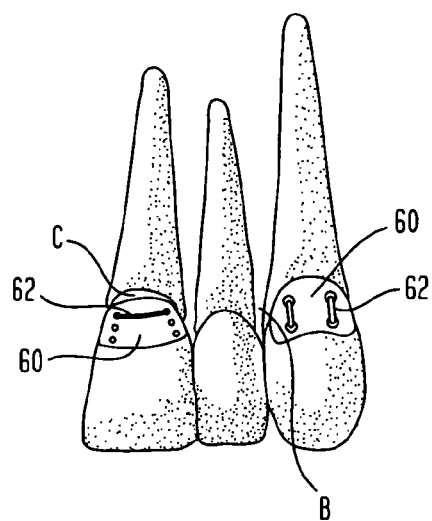
FIG. 6(c) is a side, elevational view of a portion of the anterior teeth illustrating the configurations of FIG. 6(a) fixed in situ with respect to various cervical and interproximal zones.
Figure 6D:
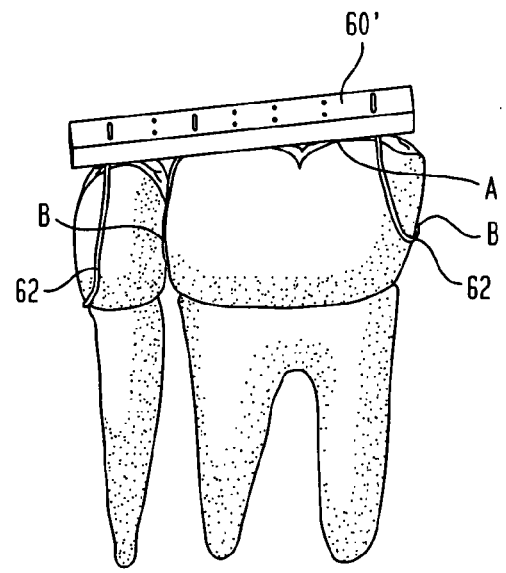
FIG. 6(d) is a side, perspective view of a portion of the posterior teeth, illustrating the configurations of FIG. 6(b) fixed in situ with respect to various occlusial and interproximal zones.

In the second configuration according to the fifth embodiment of the present invention, and referring to FIG. 6(b), the matrix is provided in the form of an occlusal corset (60'), adapted for fixation at said occlusal site (A) for at least a predetermined time period correlated to the delivery of a predetermined portion of said material to said site, as illustrated in FIG. 6(d). As with the first configuration of the fifth embodiment, the occlusal corset (60') may be made from any suitable material as described hereinbelow and is typically in the form of a table ribbon. The occlusal corset (60') may be fixed with respect to said dental surface and said site by means of one or more restraining strings or straps (62). The straps (62) are adapted for securing said corset to a tooth comprising said dental surface, and typically circumscribe at least a portion of said tooth and/or at least a portion of an adjacent tooth, as illustrated in FIG. 6(d). The straps (62) are typically made from any suitable material as described hereinbelow, and also serve as a matrix for delivering the active material to the interproximal site (B).

Thus, in the fifth embodiment, flanking strings or straps containing the active material are tied through the interproximal regions to fluoridate the interproximal regions in addition to retaining the corsets in position. The occlusal corsets (60') and the cervical corsets (60) may be prepared from long rolled ribbon tapes (with intermittent peripheral holes) that are cut to size for the appropriate usage and can also be shaped to fit the appropriate tooth anatomy, for example. Obviously the strings can also be produced as rolls and the bands outer surface can be made more resistant to degradation than the inner surface.

Optionally, the system according to the first and second embodiments may further comprise specific conventional caries stains and/or light enhanced stains (e.g. fluorescent) which are used without or with blotting agents to draw the stains after the devices are removed and the lesions restoration interface or cracks are flushed with water (see Rawls, H. R., et al., Microbiological Abs Suppl. 261, 1978; Jodaikin, A., et al., J. Oral Path 15, 1986, pp 415–418. The purpose would be to enhance interproximal caries or leakage diagnosis which remains problematic even with radiographs (see Duncan et al. JADA 126:873, 1995) and eliminate the need for irradiation.

Figure 7A:
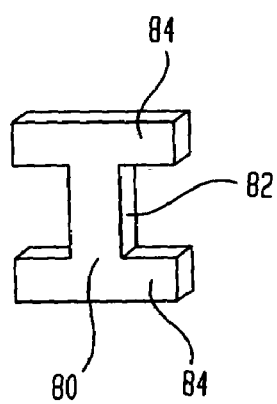
FIG. 7(a) is a front, elevational view of a sixth embodiment of the present invention.
Figure 7B:
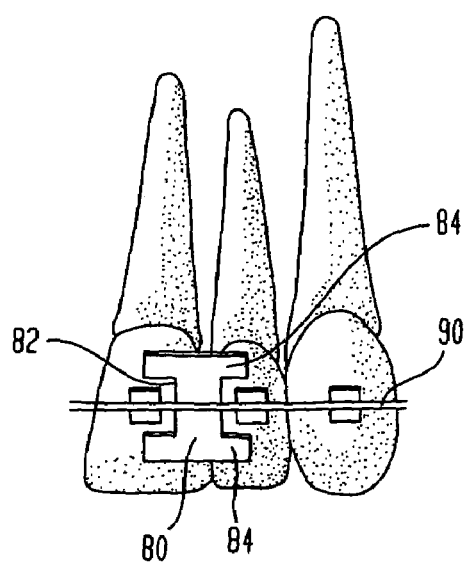
FIG. 7(b) is a side, elevational view of a portion of the anterior teeth illustrating the embodiment of FIG. 7(a) fixed in situ with respect to a labial tooth surface.

In a sixth embodiment of the present invention, and referring to FIG. 7(a), the said matrix is in the form of an interproximal "I" device (80) used in conjunction with an orthodontic device such as orthodontic arch wires. The said "I" device (80) may be fixed with respect to said dental surface and said site by positioning under the orthodontic arch wires (90), which were previously installed in the oral, cavity, as illustrated in FIG. 7(b). The vertical potion (82) of the "I" device (80) targets the interproximal areas between the adjacent teeth, while the top and bottom transverse portions (84) are optional, enabling the outer parts of the teeth to be targeted. The said "I" device (80) may be custom made in the appropriate shape, or alternatively made from a ribbon of any suitable material as described hereinbelow and cut out to the required shape and size.

Figure 8:
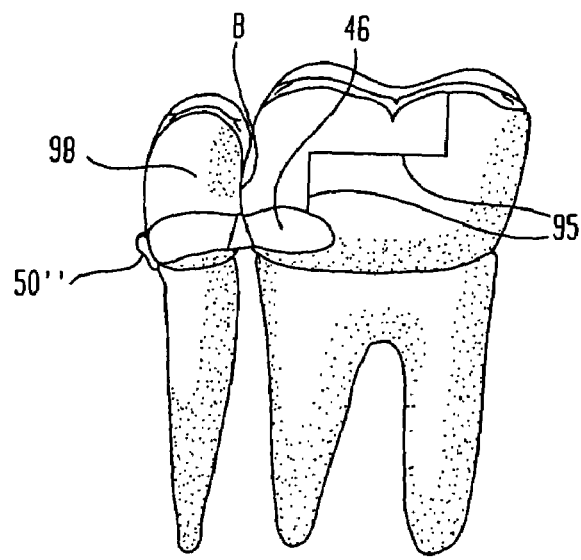
FIG. 8 is a side, elevational view of a portion of the posterior teeth, illustrating the configurations of FIG. 4(b) and FIG. 5(b) fixed in situ with respect to various interproximal and cervical zones.

The embodiments described above are not restricted for use with original dental surfaces, and thus the term "dental surface" of a tooth also includes prostheses and restoration margins of a tooth. Thus, as illustrated in FIG. 8, the second configuration of the fourth embodiment and the third configuration of the third embodiment are exemplified with respect to a tooth amalgam (98) or tooth prosthetic crown interface (95).

These applications are not limited to devices, nor are they limited to the treatment regimes described above. For example, they can be placed under gingival flaps of erupting teeth to fluoridate the tooth crown surface. In another example, the third embodiment may be used to fluoridate root canals during endodontic and restorative procedures.

Again, of course this invention is not limited to the above-described embodiments, but encompasses all the variations thereof. It is also obvious to those schooled in the art that general toxicity, allergic responses and pulp responses need to be investigated prior to applying the proposed techniques clinically.

In the system according to the present invention, the oral activity provided by the active material may be medical treatment such as fluoridization or remineralization, and/or aesthetic treatment such as providing breath fresheners, and/or any other desired activity.

Thus, the different components of the matrix of the invention can comprise a range of chemicals with the following functions:—

The Primary Active Fluoridation and/or Remineralization Agent/s or Chemical Agent/s The matrix described in this invention comprises the primary active mineralization agent which provides fluoride ions. This agent may be any single or any combination of inorganic or organic fluoride-containing pharmaceutically acceptable chemicals. These include, but are not limited to sodium fluoride, stannous fluoride, stannous hexafluorozirconate, calcium fluoride, difluorosilane, hydrogen fluoride, sodium monofluorophosphate, ytterbium trifluoride, sodium hexafluorosilicate, ammonium fluoride and amine fluorides. Preferably, the active mineralization agent is hydrogen fluoride or an amine fluoride.

Another source of fluoride ions could mimic glass ionomer cement fluoride, namely fluoroaluminosilicate glass.

The fluoride releasing agent/s is embedded within the polymeric matrix of the invention, and released therefrom in a controlled or sustained manner.

Variations in pH and salt types of fluorides (e.g. stannous, ammonium, titanium and amino fluorides) result in different retention of fluoride as calcium fluoride. For example, good results have been obtained using ammonium fluoride at pH 4.4 (see Jenkins, G. N. The Physiology and Biochemistry of the Mouth p. 495, 1978, Blackwell Scientific Publishing).

The acute lethal dose of fluoride (F) is 33 mg F/Kg body weight and the chronic toxicity can be 0.1 mg F/Kg. Thus the determination of the fluoride concentration range is governed by the size and number of devices used or the volume of material used, the duration of applying the material or device, the rate of fluoride ion release and the weight of the patient. Thus the concentrations can range from about 7–0.2%. (See A guide to the use of fluorides JADA 113:504–564,1986, prepared by the National Fluoride Task force of the NFDH).

The rate of rehardening of enamel surfaces that have been demineralized (Knoop Hardness drops from 300 to 180) with a remineralization fluoride agent (raise from 180 to 300 Knoop Hardness) is about 4 hours (see Koulourides, T., Art and Science of Dental Caries Research pp. 355–378, 1968; Poole, D. F. G. and Silverstone, L. M., Hard tissue Growth Repair and Remineralisation, pp. 35–52, Ciba Foundation Symposium No.11, Elsevier Scientific Publishing Company, 1973). Obviously the period of fluoridation required is dependent on the type of material or device herein described and its fluoride concentration as well as the type of surface or lesion being treated. Further, longer stretches of fluoridation may be more beneficial.

Although fluoride is to date the most effective remineralization agent, this invention and practice thereof is not limited to fluoride alone but may include any other remineralization agents or combination thereof, for example dissolved synthetic hydroxyapatite.

Enhancing or Other Active Agents

Enhancing agents can be added to the matrix (e.g. chlorhexidine and dicalcium phosphate dihydrate) as well as other active agents (e.g. sodium lauryl sulphate (to reduce surface tension), and xylitol).

Acidifying or Buffering Agents to Control the pH

Etching agents or buffering agents can be added to the matrix to enhance remineralization by the fluoride ions (e.g. 0.98% orthophosphoric acid pH ~3, citric acid, acidulated phosphate 0.1 mol/1 $H_3PO_4$ pH~3–4). The presence of sodium and chloride ions can increase the stability and range of fluoridation pH in some cases. Furthermore, buffers may be required to enhance cross-linkage of the matrix (for example phosphate buffers at pH 6.8). Those knowledgeable in the art will know that more than one stage of buffering may be required prior to the production of the final product in order to facilitate required steps such as cross linking or curing. Further the final product pH is also important for remineralization.

The Matrix

The role of the matrix is to carry the primary active fluoridation agent or any other enhancing or active agent and provide the required viscosity for application and/or the required stability or degradation (e.g. intraoral enzymatic biodegregation or self-generated degradation) for the delivery of the active and any auxiliary agents, in order to provide the optimal rate and time span of ion or chemical bombardment of the tooth surface and to provide a mobile environment for the fluoride ions and/or other chemicals to reach the tooth surface. Those knowledgeable and skilled in the art can alter the degradation by varying the concentrations and the degree of curing or cross-linking and type of cross-linking, or combinations thereof.

The types of possible matrices are wide. They can include agents yet unused for dental treatment and agents such as those used as denture adhesives, impression materials, temporary, provisional or permanent restorations, sutures, perio- or surgical packs and periodontal agents (see Dental Therapeutics Digest Odontos Pub Inc.: Kay L. W. Drugs in Dentistry, Bristol 1972; O'Brien, W. J. and Ryge, G. An Outline of Dental Materials, Saunders 1978; Steinberg, D et al., J. Dent Res. 67–208 Abstract No. 767, 1988; U.S. Pat. Nos. 5,324,519; 4,938,763; 5,278,201; 5,077,049; 5,739, 176; 5,733,950). The matrix materials may be sub-classified into natural products and synthetic products.

Natural Products

Polysacaccharide polymers (e.g. starch, cellulose, agar, alginates and retted flax extracts), lipids, polyisoprenes (e.g. latex rubber and gutta percha), resins and gums (e.g. tragacanth and storax) and proteins (e.g. collagen or denatured collagen in the form of gelatin) are examples.

Purified collagen can be untreated or treated with fixing agents to prolong its resistance to digestion (similar to catgut surgical suture production). Denatured collagen can be impregnated with chromium salts to prolong its tensile strength and retard its absorption. A preferred polymeric matrix is a gelatin matrix, although those experienced in the art know the method of dissolution of gelatin is highly technique-sensitive and the method used can cause considerable differences in the texture of the product ranging from jelly-like to thick and 'ropey'. Further, gelatin, like collagen, can be lysine-cross linked with glutaraldehyde (an organelle preservant which has also been used for human aortic valve implants and dental pulp treatments; Kopel, H. M. et al., J. of Dent, for Child 47: 425–430, 1980) Another possible crosslinking agent is formaldehyde, which forms intra- and intermolecular methylene bridges between various amino acids. Further examples are tannic acid and hexamethylene-diisocyanate. Again, the biocompatability of these agents must be carefully examined even though they have been used clinically. The gelatin may be of any source, for example bovine or non-mammalian gelatin. Bovine gelatin is preferably used when a matrix with higher rigidity is required.

It is prudent to note that a completely natural matrix of gelatin without crosslinking can also be used with an appropriate cover (e.g. support members as described for the first embodiment, which may be composed primarily of 1,4-polyisoprene). Furthermore, natural cross-linkings are also feasable, for example calcium and hydroxylysinorleucine, dihydroxylysinone or leucine (Traub W., and Piez, K., A. Adv. Protein Chem. 25:243–352, 1971) and dehydrodihydroxylysinonorleucine Bailey, A. J. et al., Biechem. Biophys. Res. Commun. 35:663–671 1969).

Synthetic Products

Likely candidates within the boundary of possible synthetic products that may serve for the matrices of this invention are homopolymers or copolymers with a wide molecular weight range formed by condensation, additional anionic, cationic and/or catalytic polymerization systems. Examples are cynoacrylates, polycarbonates, polyurethane, polyester urethane dimethacrylate, polycaprolactones, ethyl triglycide methacrylate, polysulphides, povidone, polyacrylic methacrylic acid, acrylic and modifications such as poly(hydroxyethyl methacrylate), poly(methylmethacrylate) modified with small amounts of ethyl butyl or other alkyl methacrylates and other carbomers. Some of these are indeed commercial products such as aqueous methacrylic polymer formulations for sustained and controlled release of dental and other products (e.g. Eudragit® Rohm). These polymers may require activators and cross-linking (see below). However, other agents are at times required, for example retarding agents such as hydroquinone and eugenol. Other yet different examples are zinc eugenolate, petrolateum and stearyl alcohol.

Cross Linking Agents

Examples are amino acids (lysine and arginine), peptides proteins, polysaccharides (e.g. dextran), lipids (e.g. sodium docusate) calcium, strontium, glutaraldehyde, formaldehyde, glycol dimethacrylate, tannic acid and allyl methacrylate.

It is to be appreciated that the degree of cross-linking is of major significance to the rate of release of the active and/or auxiliary agents. The determination of the degree of cross-linking of the polymeric matrix is within the capabilities of the man of skill in the art of pharmacy.

Liquid Vehicles

Liquid vehicles may be used particularly when preparing the matrix. Examples are water, ethyl alcohol or glycerine (glycerol) alone or in any combination, with water being preferred.

Plasticizers and Elasticizers

Plasticizers and elasticizers may be used to modify the mechanical properties of the matrix, where needed and desired. Examples are polyethylene glycol, dibutyl phthalate, glycerol, sorbitol, mineral salts, olive oil, linseed oil, light mineral oil, polymers of ethylene propylene, styrene-butadiene, vinyl ethylene acetate copolymers, butadiene isoprene, gum base and elastin (a natural rubbery protein from Ligamentum nuchae). A preferred plasticizer is sorbitol.

According to the first and second embodiments of present invention, the matrix may be made from any suitable material as described above, such as for example gelatin, in combination with an elasticizer, such as for example sorbitol and/or gum base, the gelatin being preferably cross-linked using any suitable material such as for example glutaraldehyde and/or tannic acid. Such matrices have adequate plastic properties and are at the same time of sufficient toughness to maintain the mechanical integrity of the system when affixed within the interproximal space.

According to the third embodiment of the present invention, the matrix is preferably rigid for the wedge portion, and thus typically lacks the plasticizing material of the first embodiment. Nonetheless, the wing members of this embodiment are preferably more elastic and thus may comprise a plasticizing and/or elasticizing agent.

According to the fourth, fifth and sixth embodiments the matrices, in the form of the corsets, straps and "I" members may be similar as described for the first embodiment mutatis mutandis, with the exception that in these embodiments less material or none at all may be used in the matrix.

Fillers and Softeners

The matrix may also comprise fillers and/or softeners, such as gum mastic, flour, kaolin (aluminium silicate), magnesium oxide, silicon dioxide or other various inorganic molecules are examples. It should be noted that certain ions may inhibit remineralization in some cases (for example $P_2O_7$, $HCO_3$, $SiO_4$, $CrO_4$, Mg and Zn) and some inorganic fillers can be coated with water repellant coupling agents such as vinyl silane. Examples of softeners are lecithin and waxes.

Coloring or Staining Agents

These include agents to enhance the appearance of the applied matrix, and dyes which are released to enhance caries detection, as discussed above. Examples are fuchsin or acid red 52 in propylene glycol. These diagnostic dyes include conventional histological stains, clinical decay detection agents and agents whose detection can be enhanced with light, for example fluorescence agents by UV light or other agents activated by intense light within the visual spectrum, or agents drawn by blotting of the lesion after the device or material is removed and the tooth surface rinsed.

Flavoring Agents and Breath Fresheners

Various flavoring may be added to the matrix, for example, menthol, sodium saccharin, sorbitol, aspartam, sodium chloride. Also breath fresheners may be added to the matrix, for example parsley seed, sunflower oils, and peppermint oil.

Preservatives and Sterilizing Agents

The addition of preservatives and sterilizing agents may be advantageous particularly for long-dwelling matrices, as they will inhibit the development of various microorganisms such as bacteria, fungi and yeast. Examples of preservatives are phenol, methylparaben and sorbic acid and examples of sterilizing agents are iodine, potassium and alcohol.

Hemostatic Agent

This includes vasoconstrictors (e.g. adrenalin), absorbable agents (e.g. oxidized cellulose, fibrin, calcium alginate), thromboplastic agents (e.g. thrombin), chemical agents (e.g. tannic acid, ferric chloride, zinc chloride, alum, hydrogen peroxide) or physical plugging (e.g. the device includes bone wax). The role of a hemostat would be to stop bleeding which could hamper fluoridation or chemical treatment in regions where bleeding is caused by gingival or other bleeding.

The matrix is preferably made from a material, such as for example gelatin cross-linked by tannic acid and/or glutaraldehyde, that is resorbable and/or biodegradable in the saliva by host enzymes, bacteria or by means of the dissolution properties of the saliva or drinks. Nonetheless, the matrix may alternatively be made from a non-resorbable material which also releases the active material that is being delivered to the target area. For example, the matrix may be made from rubber latex, a polymer or any one of a large variety of sugars, lipids, nucleic acids or other proteins found in rubber latex bonded to an amine fluoride which is released in the mouth because of, for example, a host enzyme.

The matrices and devices of this invention and the manufacture thereof are not limited to the hereabove chemical components, but encompasses all their variations, and include other chemicals as only examples have been presented above. Further, the biocompatability of these agents and their interactions need to be carefully examined and tested prior to clinical application.

While in the foregoing description describes in detail only a few specific embodiments of the invention, it will be understood by those skilled in the art that the invention is not limited thereto and that other variations in form and details may be possible without departing from the scope and spirit of the invention herein disclosed or exceeding the scope of the claims.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A system for the controlled delivery of at least one material having a predetermined intraoral activity to an interproximal site of at least one dental surface in an oral cavity, comprising a polymeric matrix containing said material, said system being sufficiently flexible for insertion at said interproximal site to be physically affixed thereat and sufficiently tough to maintain mechanical integrity at said site, wherein said interproximal site comprises an area of contact and surrounding surfaces between said dental surface and an adjacent dental surface.

2. A system as claimed in claim 1, wherein said matrix comprises a hydrophilic polymer that enables the matrix to be fixed by swelling in situ by the hydration thereof in the oral cavity after accommodation at said interproximal site.

3. A system as claimed in claim 2, wherein said polymeric matrix has a three dimensional form having an external surface, wherein at least a portion of said external surface is adapted for contact with at least said interproximal site of said dental surface to deliver said material to said site.

4. A system as claimed in claim 3, wherein said matrix is in the form of a disc having at least one external substantially flat surface for contact with at least said interproximal site of said dental surface to deliver said material to said site.

5. A system as claimed in claim 4, wherein said matrix is in the form of a disc having at least one external substantially concave surface for contact with at least said interproximal site of said dental surface to deliver said material to said site.

6. A system as claimed in claim 3, wherein said matrix is in the form of a pellet having at least one external substantially oval surface for contact with at least said interproximal site of said dental surface such as to deliver said material to said site.

7. A system as claimed in claim 3, wherein said matrix is in the form of a toroidal ring having at least one external substantially annular surface for contact with at least said interproximal site of said dental surface such as to deliver said material to said site.

8. A system as claimed in claim 3, wherein said matrix is in the form of a wedge having at least one external longitudinal surface for contact with at least said interproximal site of said dental surface such as to deliver said material to said site.

9. A system as claimed in claim 3, wherein said matrix is in the form of a wedge having at least one winged member at least at one longitudinal end thereof, said wedge having at least one external longitudinal surface for contact with at least said interproximal site of said dental surface such as to deliver said material to said site, and said winged member having suitable contact surfaces for delivering a portion of said material to a portion of said dental surface and an adjacent dental surface mesial and distal to said interproximal site.

10. A system as claimed in claim 1, wherein said matrix has a three dimensional form having a first external surface and a second external surface, wherein at least a portion of said first external surface is adapted for contact with at least said interproximal site of said dental surface and wherein at least a portion of said second external surface is adapted for contact with at least said interproximal site of said adjacent dental surface to deliver said material to said site.

11. A system as claimed in claim 10, wherein said matrix is in the form of a disc having opposed first and second external substantially flat surfaces for contact with at least said interproximal site of said dental surface and said adjacent dental surface, respectively, to deliver said material to said site.

12. A system as claimed in claim 10, wherein said matrix is in the form of a disc having opposed first and second external substantially concave surfaces for contact with at least said interproximal site of said dental surface and said adjacent dental surface, respectively, to deliver said material to said site.

13. A system as claimed in claim 10, wherein said matrix is in the form of a pellet having opposed first and second external substantially oval surfaces for contact with at least said interproximal site of said dental surface and said adjacent dental surface, respectively, such as to deliver said material to said site.

14. A system as claimed in claim 10, wherein said matrix is in the form of a toroidal ring having opposed first and second external substantially annular surfaces for contact with at least said interproximal site of said dental surface and said adjacent dental surface, respectively, such as to deliver said material to said site.

15. A system as claimed in claim 10, wherein said matrix is in the form of a wedge having first and second external substantially longitudinal surfaces for contact with at least said interproximal site of said dental surface and said adjacent dental surface, respectively, such as to deliver said material to said site.

16. A system as claimed in claim 10, wherein said matrix is in the form of a wedge having at least one pair of winged members at least at one longitudinal end thereof, said wedge having first and second external substantially longitudinal surfaces for contact with at least said interproximal site of said dental surface and said adjacent dental surface, respectively, such as to deliver said material to said site, and said winged members having suitable contact surfaces for delivering a portion of said material to a portion of said dental surface and to a portion of said adjacent surface mesial and distal to said interproximal site.

17. A system as claimed in claim 1, wherein said system further comprises a suitable support member for fixing said matrix to said site, said support member comprising a peripheral frame portion surrounding a net portion, said frame portion being made from a resilient material capable of enabling the support member to be accommodated at said interproximal site such as to align said net portion therewith, and wherein said net portion is adapted for accommodating said matrix and for enabling said material to be delivered therefrom to said site.

18. A system as claimed in claim 17, wherein said frame member is in the form of a ring, wherein said member is attached to the inner concave surface of said ring.

19. A system as claimed in claim 18, wherein said frame member further comprises at least one niche for facilitating gripping of the said frame member to enable affixing thereof at the interproximal site.

20. A system as claimed in claim 18, wherein said frame member further comprises at least one loop for facilitating gripping of the said frame member to enable affixing thereof at the interproximal site.

21. A system according to claim 17, wherein said support member is selected from the group consisting of natural rubber latex (cis 1,4-polyisoprene), PVC (polyvinyl chloride), Nitrile (acrylonitrile and butadiene), Neoprene (chloroprene), plastic (polyethylene) and Tactylon (styrene-based copolymers).

22. A system as claimed in claim 1, wherein said matrix is substantially biodegradable.

23. A system as claimed in claim 1, wherein said matrix is substantially resorbable.

24. A system as claimed in claim 1, wherein said matrix is substantially non-resorbable.

25. A system as claimed in claim 1, wherein said matrix is in the form of a ribbon.

26. A system as claimed in claim 25, wherein said ribbon may be joined in the form of a loop such as to circumscribe the periphery of a tooth comprising said dental surface and said site.

27. A system as claimed in claim 1, wherein said matrix is in the form of a cord.

28. A system as claimed in claim 27, wherein said cord may be joined in the form of a loop such as to circumscribe the periphery of a tooth comprising said dental surface and said site.

29. A system as claimed in claim 28, wherein said cord is made from catgut.

30. A system as claimed in claim 1, wherein said matrix is in the form of a cervical corset.

31. A system as claimed in claim 30, wherein said corset may be fixed with respect to said dental surface and said site by means of one or more restraining straps adapted for securing said corset to a tooth comprising said dental surface.

32. A system as claimed in claim 31, wherein said straps circumscribe at least a portion of said tooth.

33. A system as claimed in claim 1, wherein said matrix is in the form of an orthodontic interproximal "I" device.

34. A system as claimed in claim 33, wherein said "I" device may be fixed with respect to said dental surface and said site by means of an orthodontic arch wire previously secured in the intraoral cavity for securing said "I" device to a tooth comprising said dental surface.

35. A system for the controlled delivery of a material having a predetermined intra oral activity to an occlusal site of at least one dental surface in an oral cavity, comprising a matrix containing said matrix material; said system being sufficiently flexible for insertion at said interproximal site to be physically affixed thereat and sufficiently tough to maintain mechanical integrity at said occlusal site and adapted for affixing at said occlusal site for at least a predetermined time period correlated to the delivery of a predetermined portion of said material to said site.

36. A system as claimed in claim 35, wherein said matrix is in the form of an occlusal corset.

37. A system as claimed in claim 36, wherein said corset may be affixed with respect to said dental surface and said site by means of one or more restraining straps adapted for securing said corset to a tooth comprising said dental surface.

38. A system as claimed in claim 37, wherein said straps circumscribe at least a portion of said tooth.

39. A system as claimed in claim 38, wherein at least one said strap circumscribes at least a portion of an adjacent tooth.

40. A system as claimed in claim 1, wherein said active material is any one of inorganic or organic fluoride-containing chemical agent.

41. A system as claimed in claim 40, wherein said of material is selected from the group consisting of sodium fluoride, stannous fluoride, stannous hexafluorozirconate, calcium fluoride, difluorosilane, hydrogen fluoride, sodium monofluorophosphate, ytterbium trifluoride, sodium hexafluorosilicate, ammonium fluoride, an amine fluoride, fluoroaluminosilicate glass and any mixture thereof.

42. A system as claimed in claim 1, wherein said matrix comprises a synthetic polymer or a natural polymer selected from the group consisting of polysacaccharides, lipids, polyisoprene, gum and proteins, or any mixture thereof.

43. A system as claimed in claim 42, wherein said natural polymer is a protein selected from the group consisting of collagen and gelatin.

44. A system as claimed in claim 41, wherein said matrix comprises a synthetic polymer or a natural polymer selected from the group consisting of polysacaccharides, lipids, polyisoprene, gum and proteins, or any mixture thereof.

45. A system as claimed in claim 44, wherein said natural polymer is a protein selected from the group consisting of collagen and gelatin.

46. A system as claimed in claim 44 wherein said polymer is cross-linked.

47. A system as claimed in claim 46, wherein said polymer is cross-linked by at least one compound selected from the group consisting of glutaraldehyde, formaldehyde, glycol dimethacrylate, tannic acid and allyl methacrylate.

48. A system as claimed in claim 42, wherein said matrix further comprises an auxiliary agent selected from the group consisting of an enhancing agent for enhancing the release of the active material, platiciser, elasticiser, coloring agents, staining agent, fillers and softeners, and preserving and sterilising agents.

49. A system as claimed in claim 48, wherein said plasticiser is sorbitol.

50. A support member for fixing a polymeric matrix comprising a first material having a predetermined intraoral activity to an interproximal site of at least one dental surface in an intraoral cavity, said support member comprising a peripheral frame portion surrounding a net portion, said frame portion being made from a resilient second material capable of enabling the support member to be accommodated at said interproximal site such as to align said net portion therewith, wherein said net portion is adapted for accommodating said matrix and for enabling said first material to be delivered therefrom to said site, and wherein said support member is adapted for physical fixation at said interproximal site for at least a predetermined time period correlated to the delivery of a predetermined portion of said first material to said site.

51. A support member as claimed in claim 50, wherein said frame member is in the form of a ring, wherein said member is attached to the inner concave surface of said ring.

52. A support member as claimed in claim 50, wherein said frame member further comprises at least one niche for facilitating gripping of the said frame member to enabling affixing thereof at the interproximal site.

53. A support member as claimed in claim 50, wherein said frame member further comprises at least one loop for facilitating gripping of the said frame member to enabling affixing thereof at the interproximal site.

54. A support member according to claim 50, wherein said support member is made from a material selected from the group consisting of natural rubber latex (cis 1,4 polyisoprene), PVC (polyvinyl-chloride), Nitrile (acrylonitrile and butadiene), Neoprene (chloroprene), plastic (polyethylene) and Tactylon (styrene-based copolymers).

55. A system as claimed in claim 1, wherein said system is so constructed to be physically affixed at said interproximal site for at least a predetermined time period correlated to the delivery of a predetermined portion of said material to said site.

* * * * *

UNITED STATES PATENT AND TRADEMARK OFFICE
CERTIFICATE OF CORRECTION

PATENT NO.         : 7,118,376 B2
APPLICATION NO. : 10/221465
DATED                : October 10, 2006
INVENTOR(S)       : Ahron Jodaikin and Hilary Jodaikin It is certified that error appears in the above-identified patent and that said Letters Patent is hereby corrected as shown below:

Title page, Item (57) under Abstract, line 4, "respects" should read --respect--.
Column 2, line 17, "disadvantage" should read --disadvantages--.
Column 2, line 27, "which is also" should read --which are also--.
Column 2, line 28, "fails to reach" should read --fail to reach--.
Column 2, line 49, "exists" should read --exist--.
Column 2, line 62, "comprises" should read --comprise--.
Column 8, line 47, "embodiment if" should read --embodiment of--.
Column 9, line 25, delete "are".
Column 9, line 42, "facilitate" should read --facilitates--.
Column 10, line 42, "as for example" should read --as, for example,--.
Column 10, line 45, "embodiment" should read --embodiments--.
Column 11, line 48, after "said site" insert --.--.
Column 11, line 62, "at the of the" should read --at the--.
Column 12, line 39, "also have" should read --also has--.
Column 12, line 56, "also have" should read --also has--.
Column 15, line 59, "thereof is" should read --thereof are--.
Column 19, line 12, "While in the" should read --While the--.
Column 22, line 19, "said of material" should read --said material--.

Signed and Sealed this

Thirtieth Day of January, 2007

JON W. DUDAS
*Director of the United States Patent and Trademark Office*